United States Patent [19]

Yuan et al.

[11] Patent Number: 5,507,747
[45] Date of Patent: Apr. 16, 1996

[54] VERTEBRAL FIXATION DEVICE

[76] Inventors: Hansen A. Yuan, 5066 Pine Valley Dr., Fayetteville, N.Y. 13066; Chih-I Lin, 14292 Spring Vista La., Chino Hills, Calif. 91709

[21] Appl. No.: 420,634

[22] Filed: Apr. 12, 1995

Related U.S. Application Data

[63] Continuation of Ser. No. 207,623, Mar. 9, 1994, abandoned.

[51] Int. Cl.[6] .......................... A61B 17/70; A61B 17/84
[52] U.S. Cl. .................. 606/61; 606/72; 24/514
[58] Field of Search .................. 606/61, 60, 72, 606/74, 69; 24/514, 525, 535, 569; 403/21, 22

[56] References Cited

U.S. PATENT DOCUMENTS

| | | | |
|---|---|---|---|
| 2,676,629 | 4/1954 | Solum | 24/525 |
| 4,364,381 | 12/1982 | Sher et al. | 606/72 |
| 4,823,636 | 4/1989 | Suska | 24/514 |
| 5,067,955 | 11/1991 | Cotrel | 606/61 |
| 5,269,784 | 12/1993 | Mast | 606/69 |
| 5,334,203 | 8/1994 | Wagner | 606/69 |

Primary Examiner—Stephen C. Pellegrino
Assistant Examiner—Scott B. Markow

[57] ABSTRACT

A vertebral fixation device comprises a hooking element and a clamping element. The hooking element is provided at the top thereof with a plate portion having a fastening hole and at the bottom thereof with a hooked portion. The clamping element is provided at the bottom thereof with a fastening and clamping portion and at the top thereof with a threaded portion engageable with the fastening hole of the plate portion of the hooking element. The clamping element and the hooking element can be caused to hold securely a deformed or injured vertebra by turning and tightening the threaded portion of the clamping element.

7 Claims, 2 Drawing Sheets

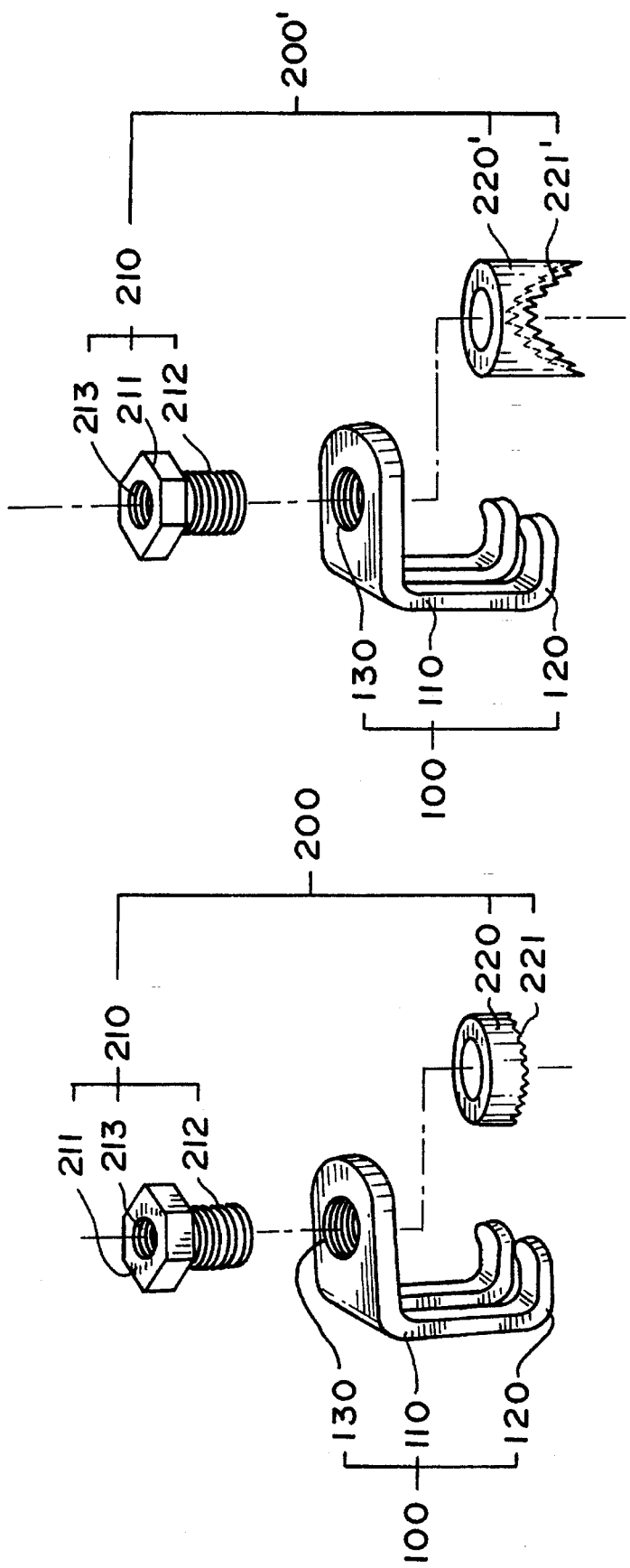

1

VERTEBRAL FIXATION DEVICE

This application is a continuation of application Ser. No. 08/207,623, filed Mar. 9, 1994, now abandoned.

FIELD OF THE INVENTION

The present invention relates generally to an orthopedic fixation device, and more particularly to a vertebral fixation device.

BACKGROUND OF THE INVENTION

The pedicle hook and the laminal hook are commonly used by the orthopedic surgeon to fix a deformed or injured vertebra. However, such fixation hooks as mentioned above are defective in design in that the pedicle hook can often inflict injuries on the bone tissue of the deformed or injured vertebra onto which the pedicle hook is fastened, and that the laminal hook is a poor fastener.

SUMMARY OF THE INVENTION

It is therefore the primary objective of the present invention to provide a vertebral fixation device which is an excellent fastener and does not cause structural damage to the bone tissue of a vertebra onto which the vertebral fixation device is fastened.

It is another objective of the present invention to provide a vertebral fixation device capable of hooking and clamping simultaneously a vertebra under treatment.

It is still another objective of the present invention to provide a vertebral fixation device made up of a hooking element and a clamping element. The foregoing objectives of the present invention are attained by the vertebral fixation device, which comprises a hooking element and a clamping element. The hooking element is composed of a plate portion located at the top portion thereof and provided with a threaded hole, and of a hooked portion located at the bottom portion thereof. The top portion mentioned above refers to the portion opposite in direction to the bottom portion which is the portion facing a vertebra to be fixed.

The clamping element is provided at the bottom thereof with a fastening and clamping portion and at the top thereof with a threaded portion having threads engageable with the threaded hole of the hooking element. The bottom mentioned above refers to the portion that faces the vertebra to be fixed while the top mentioned above refers to the portion that is opposite to the bottom.

The vertebral fixation device of the present invention is characterized in that the hooking element and the clamping element can be caused to work together to hold securely a deformed or injured vertebra by rotating appropriately the threaded portion of the clamping element in the threaded hole of the hooking element.

All elements of the vertebral fixation device of the present invention described above are made of materials biocompatible with the human body, such as the iron-based material like stainless steel 316 LVM, the titanium-based material like Ti-6-4 nickel chromium alloy, etc.

Preferably, the plate portion and the hooked portion of the hooking element of the present invention described above are made integrally, with the hooked portion having preferably a plurality of hooks for use in fastening with the upper fringes of both sides of the vertebral arch root.

The threaded portion and the fastening and clamping portion of the clamping element of the present invention described above may be made integrally or riveted; nevertheless they are preferably riveted in view of the fact that the action of rotating the threaded portion can result in a change in the distance between the hooked portion and the fastening and clamping portion without actuating the fastening and clamping portion to turn along with the threaded portion. As the threaded portion is tightened gradually, the hooked portion of the hooking element and the fastening and clamping portion of the clamping element work together to hold securely a vertebra to be fixed. In addition, the vertebra is further fixed securely by the threaded portion which takes hold of the fastening and clamping portion.

The fastening and clamping portion of the clamping element described above may be of any shape, preferably a disklike shape. The bottom of the fastening and clamping portion is fastened with the vertebra and provided with a planar surface or a curve surface in conformity with the curvature of the vertebra. It is suggested that the planar surface or the curve surface is serrated to enhance the fastening effect of the fastening and clamping portion of the clamping element of the present invention.

The fixation device of the present invention described above may be provided with a connecting element, which is intended for use in fastening the fixation device described above with other vertebral fixation device. For example, the threaded portion of the clamping element has a head provided with a threaded hole engageable with another fixation device. The foregoing objectives, structures, functions and features of the present invention will be more readily understood by studying the following detailed description of the preferred embodiments of the present invention in conjunction with the drawings provided herewith.

BRIEF DESCRIPTION OF THE DRAWINGS

FIG. 1 shows an exploded view of a first preferred embodiment of the present invention.

FIG. 2 shows an exploded view of a second preferred embodiment of the present invention.

DETAILED DESCRIPTION OF THE INVENTION

Figure 3:
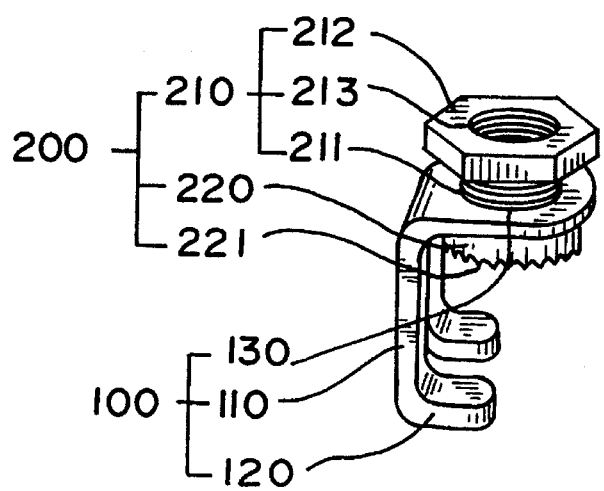
FIG. 3 shows a perspective schematic view of the first preferred embodiment in combination, according to the present invention.

As shown in FIG. 1, a vertebral fixation device of the first preferred embodiment of the present invention comprises a hooking element 100 and a clamping element 200. The hooking element 100 is composed of a plate portion 110, a hooked portion 120, and a threaded hole 130. The clamping portion 200 is made up of a threaded portion 210 and a fastening and clamping portion 220, with the threaded portion 210 having a head 211, threads 212 and a fastening hole 213, and with the fastening and clamping portion 220 having a serrated portion 221.

The second preferred embodiment of the present invention is shown in FIG. 2 in which the reference numerals are similar in definition to those of the first preferred embodiment as shown in FIG. 1. The second preferred embodiment is different from the first preferred embodiment in that the former has the fastening and clamping portion 220' provided with a curve bottom 221' facing a vertebra and having a curvature in conformity with the curvature of the vertebra onto which the curve bottom 221' is fastened. It must be noted here that the fastening and clamping portion 220 of the first preferred embodiment, as shown in FIG. 1, is provided with a planar bottom facing a vertebra and having the serrated portion 221 which is fastened onto the vertebra.

The first preferred embodiment, as shown in FIG. 1, is shown in combination in FIG. 3 in which the reference numerals are similar in definition to those of FIG. 1. As shown in FIG. 3, the threaded portion 210 and the fastening and clamping portion 220 are riveted.

Figure 4:
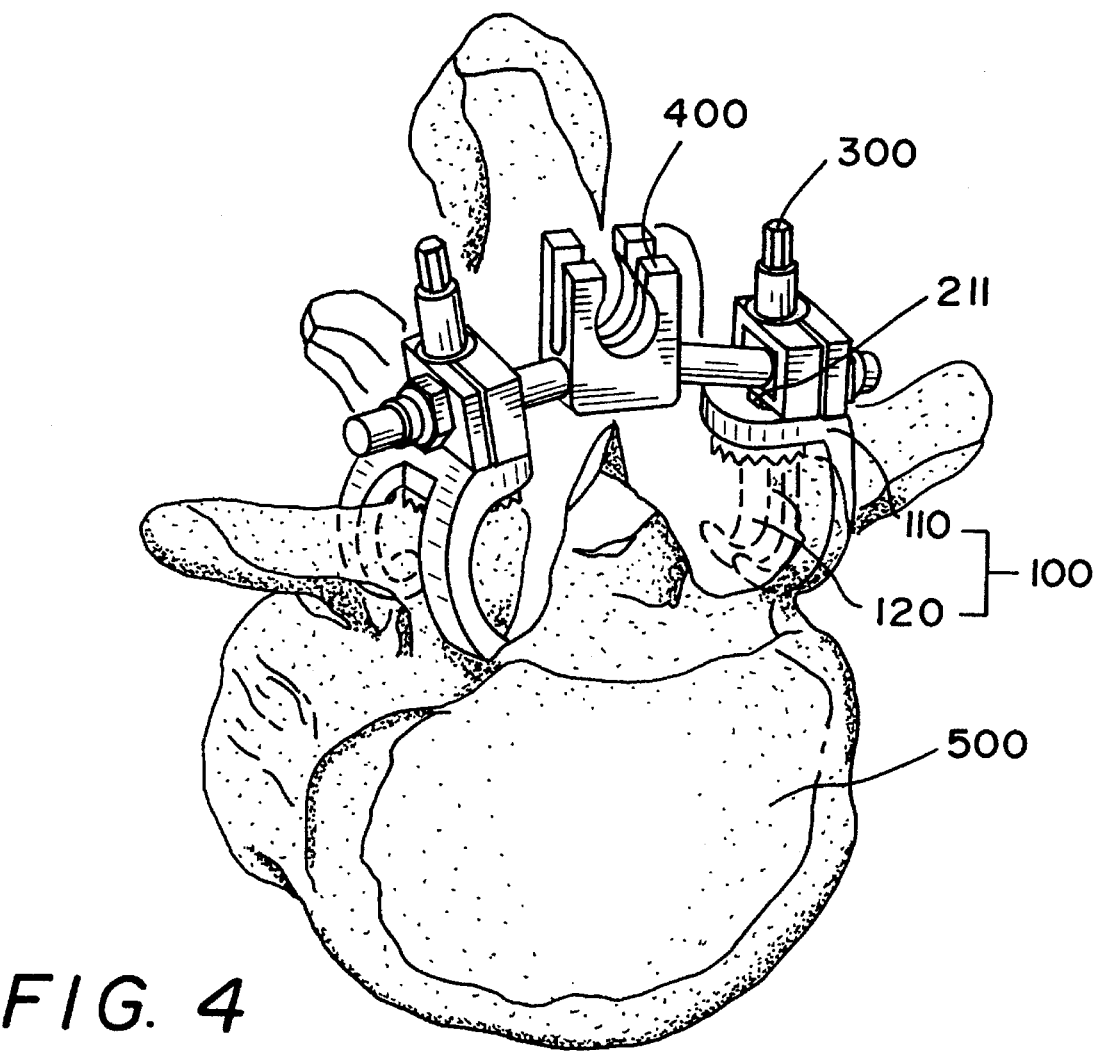
FIG. 4 is a schematic view showing the first preferred embodiment of the present invention, as shown in FIG. 1, fastened with a vertebra intended to be fixed.

In an orthopedic surgery treating a deformed or injured vertebra, the vertebral fixation device of the present invention may be employed in combination with another vertebral fixation device, as shown in FIG. 4 in which the reference numerals, such as 100, 110, 120 and 211, are similar in definition to those of FIG. 1. As shown in FIG. 4, a deformed vertebra 500 is fixed by means of the vertebral fixation device of the present invention and another vertebral fixation device 400 which is coupled with the fixation device of the present invention by a fastening screw 300 engaging the fastening hole 213 of the head 211 of the clamping element 200.

The embodiments of the present invention described above are to be regarded in all respects as merely illustrative and not restrictive. Accordingly, the present invention may be embodied in other specific forms without deviating from the spirit thereof. The present invention is therefore to be limited only by the scope of the following appended claims.

What I claim is:

1. A vertebral fixation device comprising:

a unitary hooking element provided at a top thereof with a plate portion having a threaded hole and at a bottom thereof with a plurality of hooked portions adapted to be fastened to upper fringes of opposing sides of a vertebral arch root, said plate and hooked portions being integrally formed; and a clamping element provided at a bottom thereof with a fastening and clamping portion, said fastening and clamping portion lying between the plate portion and the hooked portions of said hooking element and being adapted to face a vertebra, said clamping element being further provided at a top thereof with a threaded portion having threads threadably engaged with said threaded hole of said plate portion of said hooking element;

the threaded portion of said clamping element being threaded into the threaded hole of said plate portion of said hooking element and the fastening and clamping portion being attached to the clamping element, such that said hooking element and said clamping element can be caused to hold securely a vertebra by engaging the hooked portions of the hooking element with the vertebra and then turning and tightening said threaded portion of said clamping element until the fastening and clamping portion is tightened upon the vertebra such that the vertebra is sandwiched between the hooked portions of the hooking element and the fastening and clamping portion of said clamping element.

2. The vertebral fixation device of claim 1 wherein said threaded portion of said clamping element and said fastening and clamping portion of said clamping element are riveted.

3. The vertebral fixation device of claim 1 wherein said fastening and clamping portion of said clamping element has a serrated surface adapted to face and engage a vertebra.

4. The vertebral fixation device of claim 3 wherein said threaded portion of said clamping element has a head provided with a threaded hole engageable with another vertebral fixation device.

5. The vertebral fixation device of claim 1 wherein said fastening and clamping portion of said clamping element has a curved surface adapted to face a vertebra and having a curvature in conformity with a curvature of that vertebra.

6. The vertebral fixation device of claim 5 wherein said threaded portion of said clamping element has a head provided with a threaded hole engageable with another vertebral fixation device.

7. The vertebral fixation device of claim 1 wherein said threaded portion of said clamping element has a head provided with a threaded hole engageable with another vertebral fixation device.

* * * * *